(12) United States Patent
Hall et al.

(10) Patent No.: US 10,376,347 B2
(45) Date of Patent: Aug. 13, 2019

(54) ATTACHMENT FOR AN ELECTRIC TOOTHBRUSH HANDLE AND METHOD OF ATTACHING

(71) Applicant: KONINKLIJKE PHILIPS N.V., Eindhoven (NL)

(72) Inventors: Scott E. Hall, Issaquah, WA (US); Raviteja Senadhipathi, Eindhoven (NL); Barath Kumar Soundararajan, Coimbatore (IN); Dharshan Manjunath, Laxmipura (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 520 days.

(21) Appl. No.: 15/029,833

(22) PCT Filed: Oct. 23, 2014

(86) PCT No.: PCT/IB2014/065562
§ 371 (c)(1),
(2) Date: Apr. 15, 2016

(87) PCT Pub. No.: WO2015/059660
PCT Pub. Date: Apr. 30, 2015

(65) Prior Publication Data
US 2016/0250010 A1 Sep. 1, 2016

Related U.S. Application Data

(60) Provisional application No. 61/895,428, filed on Oct. 25, 2013.

(51) Int. Cl.
*A61C 17/22* (2006.01)

(52) U.S. Cl.
CPC .......... *A61C 17/222* (2013.01); *A61C 17/225* (2013.01); *Y10T 403/7018* (2015.01); *Y10T 403/7021* (2015.01); *Y10T 403/7022* (2015.01)

(58) Field of Classification Search
CPC ..... A61C 17/222; A61C 17/225; A61C 17/22; A61C 17/32; A61C 17/34; A61C 17/24;
(Continued)

(56) References Cited

U.S. PATENT DOCUMENTS 5,289,604 A 3/1994 Kressner
2003/0101526 A1 6/2003 Hilscher et al.
(Continued)

FOREIGN PATENT DOCUMENTS

DE 102005041459 A1 3/2007
WO 0076420 A1 12/2000
(Continued)

*Primary Examiner* — Sean K. Hunter
*Assistant Examiner* — Aaron R McConnell (57) ABSTRACT

An attachment mountable to an electric toothbrush handle having a drive shaft comprises a neck member having an elongated body with a principal axis and a cavity; a slide member with an engagement surface; a guide sleeve member having a cavity, a first outer surface with an engagement opening, and a transition surface; and a collar member. The guide sleeve member, with slide member inserted within the engagement opening, is inserted within the neck member cavity. Insertion of the drive shaft into the collar member and guide sleeve member from a first radial position along an axis offset and parallel to the principal axis to a second radial position in-line with the principal axis, via the transition surface, results in the drive shaft being held in frictional contact with the engagement surface of the slide member to enable transfer of force/motion from the drive shaft to the neck member.

13 Claims, 9 Drawing Sheets

(58) Field of Classification Search
CPC ....... A61C 17/26; B24B 45/006; F16D 1/104; F16D 1/08; F16D 1/10; Y10T 403/7064; Y10T 403/7018; Y10T 403/7021; Y10T 403/7024; Y10T 403/7098; A46B 13/02; B25B 23/0007; B25B 23/16
USPC .................................. 15/22.1; 403/313, 314
See application file for complete search history.

(56) References Cited

U.S. PATENT DOCUMENTS

| | | |
|---|---|---|
| 2010/0043156 A1 | 2/2010 | Kressner |
| 2010/0101032 A1* | 4/2010 | Kressner ................ A61C 17/22 15/22.1 |
| 2010/0162498 A1 | 7/2010 | Kressner |
| 2010/0162501 A1 | 7/2010 | Kressner |
| 2010/0251493 A1* | 10/2010 | Sale ..................... A61C 17/222 15/22.1 |
| 2011/0083288 A1* | 4/2011 | Kressner .............. A61C 17/222 15/22.1 |

FOREIGN PATENT DOCUMENTS

| | | |
|---|---|---|
| WO | 2005046506 A1 | 5/2005 |
| WO | 2013009363 A1 | 1/2013 |
| WO | 2013061219 A1 | 5/2013 |

* cited by examiner

ATTACHMENT FOR AN ELECTRIC TOOTHBRUSH HANDLE AND METHOD OF ATTACHING

CROSS-REFERENCE TO PRIOR APPLICATIONS

This application is the U.S. National Phase application under 35 U.S.C. § 371 of International Application No. PCT/IB2014/065562, filed on Oct. 23, 2014, which claims the benefit of U.S. Provisional Patent Application No. 61/895,428, filed on Oct. 25, 2013. These applications are hereby incorporated by reference herein.

The present embodiments relate generally to electric toothbrushes and more particularly, to an attachment or brush head assembly for an electric toothbrush handle having a drive shaft and a method of attaching.

A brush head portion of an electric powered toothbrush typically has a much shorter useful life than a remainder of the electric toothbrush, i.e., the handle portion, which generally includes a drive shaft, control and power assemblies of the electric toothbrush appliance. The brush head must be both convenient to remove and insert onto the drive shaft of the electric toothbrush, but also must be able to reliably transfer the force of the drive shaft to the brush head with a minimum loss of motion. A large number of different structural arrangements have been used to accomplish these two different and somewhat conflicting requirements. In most cases, the brush head simply has a single configuration which accomplishes both results, i.e., it has a tight enough fit to provide the required force transfer and which can be pulled on and off the drive member (drive shaft) with a reasonable amount of force exerted by a typical user.

Accordingly, an improved method and apparatus for overcoming the problems in the art is desired.

In accordance with one aspect, a toothbrush neck assembly is disclosed which includes a connecting arrangement in which the toothbrush neck assembly achieves (i) both radial and axial motion simultaneously and (ii) establishes sufficient frictional contact between the electric toothbrush handle drive shaft and a slide member of the toothbrush neck assembly. Frictional force generated via the frictional contact ensures reliable transfer of force/motion from the drive shaft member to the toothbrush neck assembly.

In accordance with another aspect, an attachment mountable to a handle having a drive shaft comprises a neck member, a slide member, and a guide sleeve member. The neck member comprises an elongated body with a principal axis, the elongated body having a cavity extending within the elongated body from a distal end of the neck member. The slide member comprises (i) an engagement surface and (ii) a linear displacement surface, opposite the engagement surface. The guide sleeve member comprises an elongated body having a cavity extending within the elongated body from a distal end of the guide sleeve member. The guide sleeve member further comprises (i) a first outer surface with an engagement opening disposed inward and transverse to the elongated body, and (ii) a second outer surface, opposite the first outer surface, that comprises a transition surface. The slide member is adapted for moveable insertion, engagement surface first, within the engagement opening of the guide sleeve member and extendable within the guide sleeve member cavity. The guide sleeve member, together with moveably inserted slide member, is adapted for moveable insertion, proximal end first, within the cavity of the neck member. Responsive to insertion of the drive shaft into the cavity of the guide sleeve member together with the moveably inserted slide member within the cavity of the neck member from (a) a first radial position along an axis offset and parallel to the principal axis to (b) a second radial position in-line with the principal axis, via the transition surface, the drive shaft is held in frictional contact with the engagement surface of the slide member. The frictional contact enables a reliable transfer of at least one of force and motion from the drive shaft to the neck member.

In accordance with another aspect, an attachment mountable to an electric toothbrush handle having a drive shaft is provided. The attachment comprises a neck member, a slide member, a guide sleeve member, and a collar member. The neck member comprises at least a toothbrush neck and having an elongated body with a principal axis, the elongated body having a cavity extending within the elongated body from a distal end of the neck member. The slide member comprises (i) an engagement surface and (ii) a linear displacement surface, opposite the engagement surface. The guide sleeve member comprises an elongated body, the elongated body having a cavity extending within the elongated body from a distal end of the guide sleeve member. The guide sleeve member further comprises (i) a first outer surface with an engagement opening disposed inward and transverse to the elongated body, and (ii) a second outer surface, opposite the first outer surface, that comprises a transition surface. The slide member is adapted for moveable insertion, engagement surface first, within the engagement opening of the guide sleeve member and extendable within the guide sleeve member cavity. The guide sleeve member together with moveably inserted slide member is adapted for moveable insertion, proximal end first, within the cavity of the neck member. In addition, the collar member comprises a body with a cavity extending therein between a proximal end to a distal end. The proximal end of the collar member is configured to be fixedly attached to the distal end of the neck member for removeably securing the slide member and guide sleeve member within the neck member. Responsive to insertion of the drive shaft into the cavity of the collar member and the cavity of the guide sleeve member together with the moveably inserted slide member within the cavity of the neck member from (a) a first radial position along an axis offset and parallel to the principal axis to (b) a second radial position in-line with the principal axis, via the transition surface, the drive shaft is held in frictional contact with the engagement surface of the slide member to enable a reliable transfer of at least one of force and motion from the drive shaft to the neck member.

In accordance with yet another aspect, a method for mounting an attachment to an electric toothbrush handle having a drive shaft is provided. The method comprises providing a neck member having an elongated body with a principal axis, the elongated body having a cavity extending within the elongated body from a distal end of the neck member; providing a slide member having (i) an engagement surface and (ii) a linear displacement surface, opposite the engagement surface; providing a guide sleeve member having an elongated body, the elongated body having a cavity extending within the elongated body from a distal end of the guide sleeve member, the guide sleeve member further having (i) a first outer surface with an engagement opening disposed inward and transverse to the elongated body, and (ii) a second outer surface, opposite the first outer surface, that comprises a transition surface, wherein the slide member is adapted for moveable insertion, engagement surface first, within the engagement opening of the guide sleeve member and extendable within the guide sleeve member cavity, the guide sleeve member together with moveably inserted slide member being adapted for moveable insertion, proximal end first, within the cavity of the neck member; and inserting the drive shaft into the cavity of the guide sleeve member together with the moveably inserted slide member within the cavity of the neck member from (a) a first radial position along an axis offset and parallel to the principal axis to (b) a second radial position in-line with the principal axis, via the transition surface, wherein the drive shaft is held in frictional contact with the engagement surface of the slide member to enable a reliable transfer of at least one of force and motion from the drive shaft to the neck member.

In accordance with yet another aspect, the method further comprises removeably securing, via a collar member, the slide member and guide sleeve member within the neck member, wherein the collar member comprises a body with a cavity extending therein between a proximal end to a distal end, and wherein removeably securing includes fixedly attaching the proximal end of the collar member to the distal end of the neck member.

The embodiments of the present disclosure advantageously solve the problem of motion loss between and handle drive shaft and brush head due to high operating frequency and vibrations.

Another advantage resides in the mechanism according to the embodiments of the present disclosure which advantageously allows for easy insertion/removal of the brush head from the drive shaft with minimal efforts.

Still further advantages and benefits will become apparent to those of ordinary skill in the art upon reading and understanding the following detailed description.

The embodiments of the present disclosure may take form in various components and arrangements of components, and in various steps and arrangements of steps. Accordingly, the drawings are for purposes of illustrating the various embodiments and are not to be construed as limiting the embodiments. In the drawing figures, like reference numerals refer to like elements. In addition, it is to be noted that the figures may not be drawn to scale.

FIG. 2 (2A, 2B, 2C) is a combined top, side, and perspective views of a slide member of an attachment according to an embodiment of the present disclosure;

FIG. 3 (3A, 3B, 3C) is a combined sectional view along an elongated body of the neck member, sectional view transverse to the elongated body of the neck member, and a side view of the neck member according to an embodiment of the present disclosure;

FIG. 4 (4A, 4B) is a combined side and perspective views of a drive shaft of an electric toothbrush handle according to an embodiment of the present disclosure;

FIG. 5 (5A-5F) is a combined right perspective, left perspective, left side, sectional view along an elongated body of the guide sleeve member, transition side, and sectional view transverse to the elongated body of the guide sleeve member according to an embodiment of the present disclosure;

FIG. 6 (6A, 6B, 6C) is a combined side, top, and perspective views of the collar member according to an embodiment of the present disclosure;

FIG. 7 (7A, 7B, 7C, 7D) is a combined exploded perspective views at various stages of assembly of component parts of the attachment according to an embodiment of the present disclosure;

FIG. 8 (8A, 8B, 8C, 8D) is a combined sectional views of various stages of insertion of the drive shaft into the attachment or brush neck assembly according to an embodiment of the present disclosure; and FIG. 9 (9A, 9B, 9C, 9D) is a combined sectional views of various stages of removal of the drive shaft from the attachment or brush neck assembly according to an embodiment of the present disclosure.

The embodiments of the present disclosure and the various features and advantageous details thereof are explained more fully with reference to the non-limiting examples that are described and/or illustrated in the drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the present disclosure. The examples used herein are intended merely to facilitate an understanding of ways in which the embodiments of the present may be practiced and to further enable those of skill in the art to practice the same. Accordingly, the examples herein should not be construed as limiting the scope of the embodiments of the present disclosure, which is defined solely by the appended claims and applicable law.

It is understood that the embodiments of the present disclosure are not limited to the particular methodology, protocols, devices, apparatus, materials, applications, etc., described herein, as these may vary. It is also to be understood that the terminology used herein is used for the purpose of describing particular embodiments only, and is not intended to be limiting in scope of the embodiments as claimed. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which the embodiments of the present disclosure belong. Preferred methods, devices, and materials are described, although any methods and materials similar or equivalent to those described herein can be used in the practice or testing of the embodiments.

According to one embodiment, an attachment for an electric toothbrush includes a toothbrush neck and connecting assembly that is insert-able onto an electric toothbrush handle drive shaft. The connecting assembly includes a slide member that slides in a slot within the toothbrush neck, along with a guide sleeve. The toothbrush neck and connecting assembly is inserted and moved axially on to the handle drive shaft along an axis of the guide sleeve until an internal conical tapered surface of the toothbrush neck rides over a complementary external tapered surface of the guide sleeve. Riding over the external conical tapered surface of the guide sleeve imparts radial movement to the toothbrush neck and connecting assembly. The imparted radial movement establishes a frictional contact between a flat engagement surface of the slide member and a flat surface within a notch of the drive shaft. The frictional contact between the slide member and the drive shaft enables a positive transfer of force/motion from the drive shaft to the toothbrush neck and connecting assembly.

Figure 1:
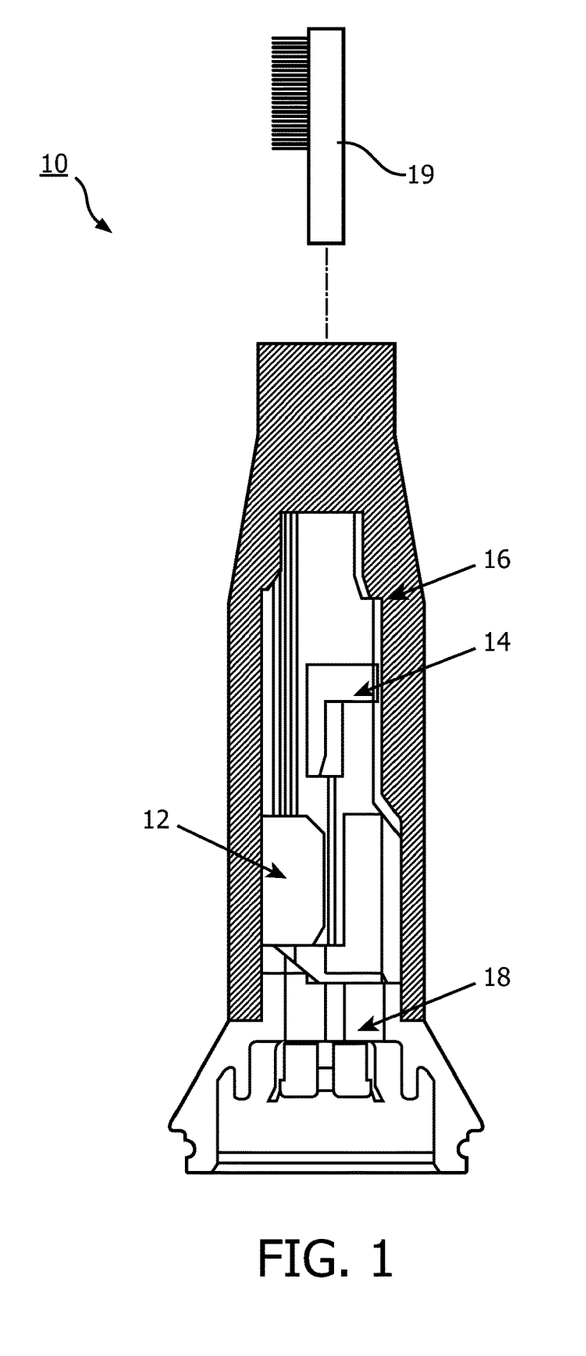
FIG. 1 is a sectional view of the assembled attachment or brush neck assembly according to an embodiment of the present disclosure.

According to an embodiment of the present disclosure, an attachment 10 comprises a slide member 12, a guide sleeve member 14, a neck member 16 and a collar member 18, as shown in the sectional view of the assembled attachment of FIG. 1. In one embodiment, the attachment 10 comprises a toothbrush neck assembly including a brush 19 for use with an electric toothbrush handle having a drive shaft (not shown).

Figure 2A:
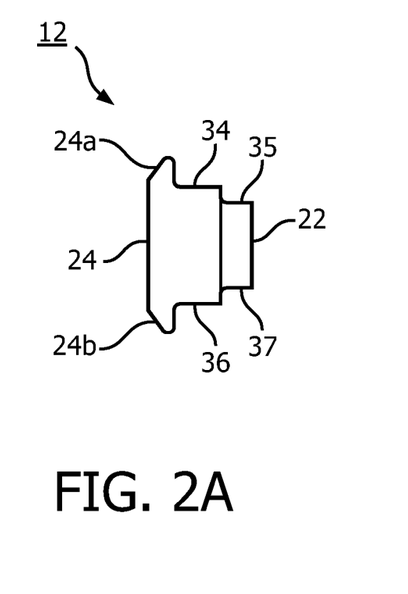
Figure 2B:
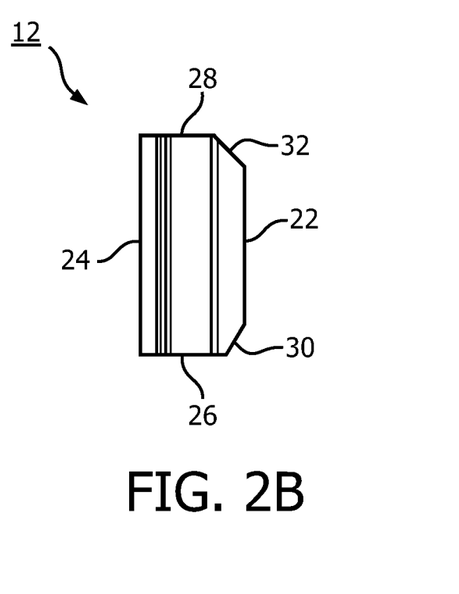
Figure 2C:
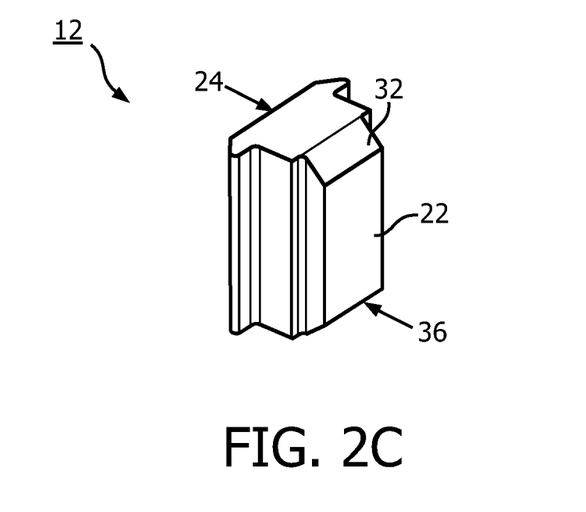

Turning now to FIG. 2, there is shown a top view FIG. 2A, a side view FIG. 2B, and a perspective view FIG. 2C of the slide member 12 of the attachment 10 according to an embodiment of the present disclosure. The slide member 12 comprises an engagement surface 22 and a linear displacement surface 24, opposite the engagement surface 22. As will be discussed further herein, the engagement surface 22 is configured for being held in frictional contact with a drive shaft of an electric toothbrush handle to enable a reliable transfer of at least one of force and motion from the drive shaft to the neck member 16. In one embodiment, the engagement surface 22 of slide member 12 is configured for being held in frictional contact with a flat surface of a notch in the drive shaft, as will be discussed further herein below.

The linear displacement surface 24 extends along a length dimension of the slide member 12, between first and second abutment surfaces (26, 28) at respective ends of slide member 12. Linear displacement surface 24 further includes projections (24a, 24b) extending along sides of the linear displacement surface proximate a first set of side surfaces (34, 36). In one embodiment, the linear displacement surface 24 and projections (24a, 24b) are configured for being moveably fitted within a slot that extends along a first surface of a first pair of inner surfaces of a cavity of the neck member 16, as will be discussed further herein below. Slide member 12 further comprises forward and rearward slant surfaces (30, 32) extending between a respective abutment surface at an corresponding end of the slide member 12 and the engagement surface 22, as shown in FIGS. 2B and 2C. In addition, slide member 12 comprises first and second sets of side surfaces (34, 36) and (35, 37) along a length dimension of slide member 12.

Figure 3A:
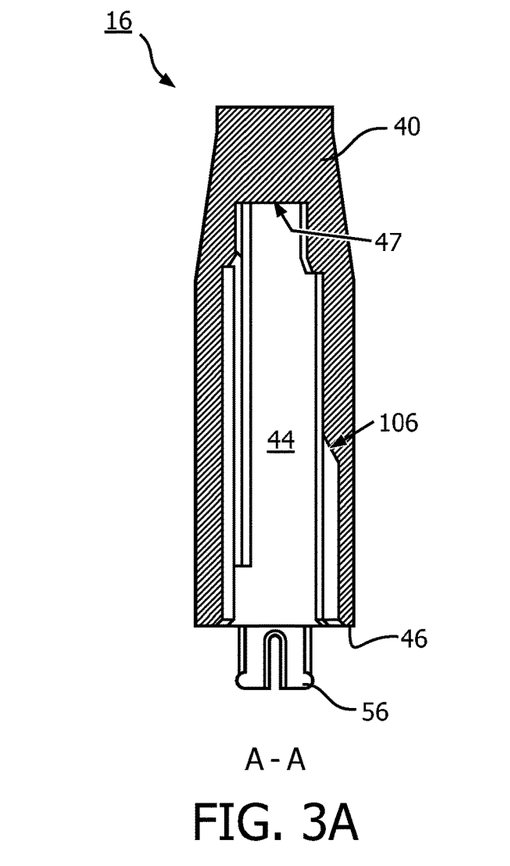
Figure 3B:
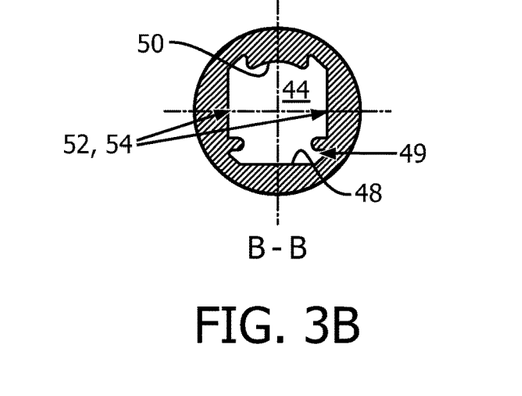
Figure 3C:
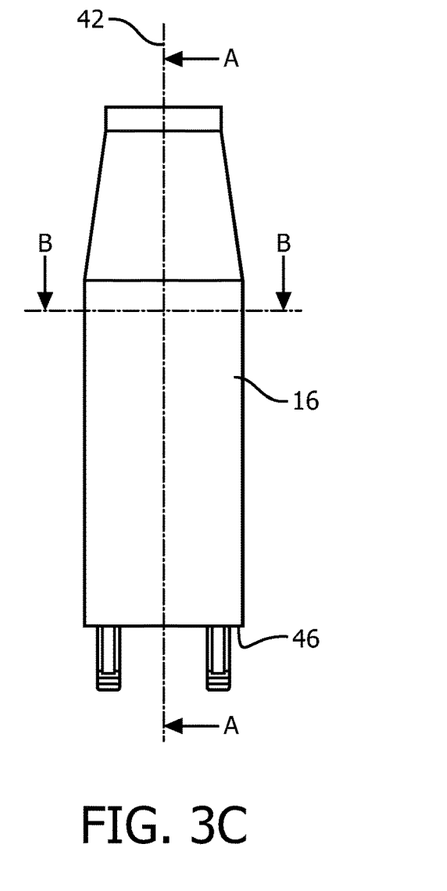

With reference now to FIG. 3, there is shown a sectional view FIG. 3A along line A-A of an elongated body 40 of the neck member 16, a sectional view FIG. 3B along line B-B transverse to the elongated body 40 of the neck member 16, and a side view FIG. 3C of the neck member 16 according to an embodiment of the present disclosure. In one embodiment, the neck member 16 comprises an elongated body 40 with a principal axis 42, the elongated body 40 having a cavity 44 extending within the elongated body from a distal end 46 of the neck member 16. In one embodiment, the cavity 44 extends within the elongated body from the distal end 46 to an inner abutment or end surface 47, towards a proximal end of the neck member 16. In another embodiment, the elongated body 40 of neck member 16 comprises a cylindrically shaped elongated body.

In addition, cavity 44 of neck member 16 provides for at least two axes parallel to the principal axis 42 and defined in part by first and second pairs of inner surfaces (48, 50) and (52, 54) along a length dimension of the cavity 44.

The first pair of inner surfaces (48, 50) comprises a first surface 48 and a second surface 50, opposite the first surface, within the cavity 44 of the neck member 16. The first surface 48 further comprises a linear translation surface having a slot that extends along the first surface and is adapted for moveably fitting the linear displacement surface 24 of the slide member 12 therein, wherein the engagement surface 22 of the slide member 12 is maintained at a given radial distance from the principal axis 42 in response to the guide sleeve member 14 together with the moveably inserted slide member 12 being moveably fitted within the cavity 44 of the neck member 16, as will be discussed further herein below. The second surface 50 comprises a transition surface configured to complement a transition surface of the guide sleeve member 14 and to enable a drive shaft to be moveably fitted between the first and second radial positions via the transition surface of the guide sleeve member 14 in response to the guide sleeve member being moveably fitted within the cavity 44 of the neck member 16, as will be discussed further herein below.

The second pair of inner surfaces (52, 54) along the length dimension of the cavity 44 comprise guide surfaces for a second pair of outer surfaces of the guide sleeve member 14, wherein the second pair of outer surfaces of the guide sleeve member 14 are maintained centered about the principal axis 42 of the neck member 16 in response to the guide sleeve member 14 being moveably fitted within the cavity 44 of the neck member 16.

With reference to FIGS. 3A and 3C, the neck member 16 further comprises at least one pair of resilient attachment tabs 56 at the distal end 46 of the neck member 16. The at least one pair of resilient attachment tabs 56 is configured for insertion into at least one attachment aperture at the proximal end of the collar member 18, wherein the neck member 16 and collar member 18 become fixedly attached to one another, as will be discussed further herein below.

In one embodiment, the neck member 16 comprises a toothbrush neck and connecting assembly adapted for insertion onto the drive shaft of an electric toothbrush handle.

Figure 4A:
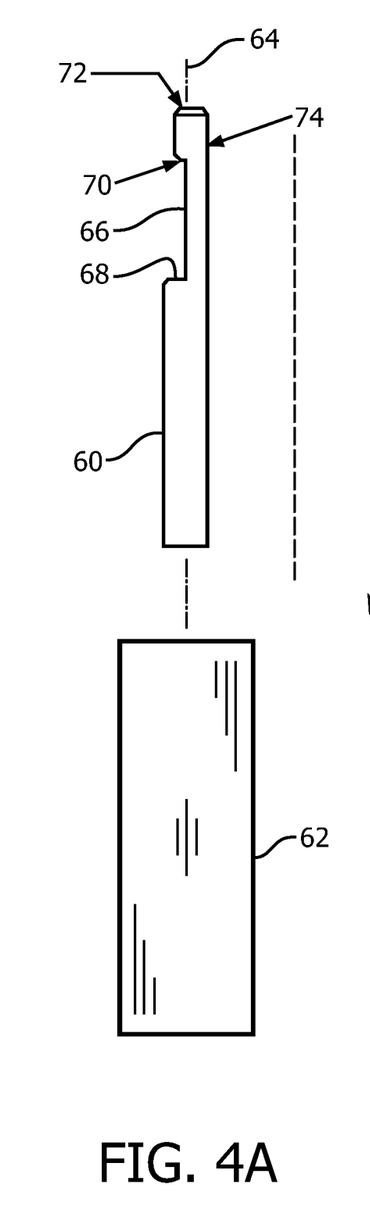
Figure 4B:
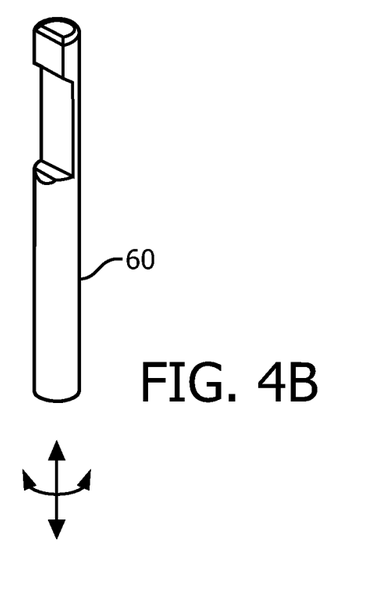

With reference now to FIG. 4, there is shown a side view FIG. 4A and a perspective view FIG. 4B of a drive shaft 60 of an electric toothbrush handle 62 according to one embodiment of the present disclosure. Drive shaft 60 comprises a generally cylindrical shaft having a principal axis 64 and is coupled, at a distal end thereof, to a suitable motor or actuator (not shown) within handle 62 for providing at least one of force and motion, including at least one of translational and rotational force/motion along and/or about the drive shaft, as indicated by the corresponding translational/rotational arrows in FIG. 4B. Drive shaft 60 includes a notch 66 disposed along a length dimension thereof, the notch having a generally flat surface. The ends (68, 70) of notch 66 include abutment surfaces, wherein the abutment surfaces 68 and 70 further comprise partial slanted faces. In addition, in one embodiment, the proximal end 72 of drive shaft 60 includes a top flat face. In another embodiment, drive shaft 60 further includes a flat surface that extends along a length dimension of the drive shaft, between the notch 66 and proximal end 72. In one embodiment, the flat surface 74 is parallel to the principal axis 64 and parallel to the flat surface of notch 66.

Figures 5A, 5B:
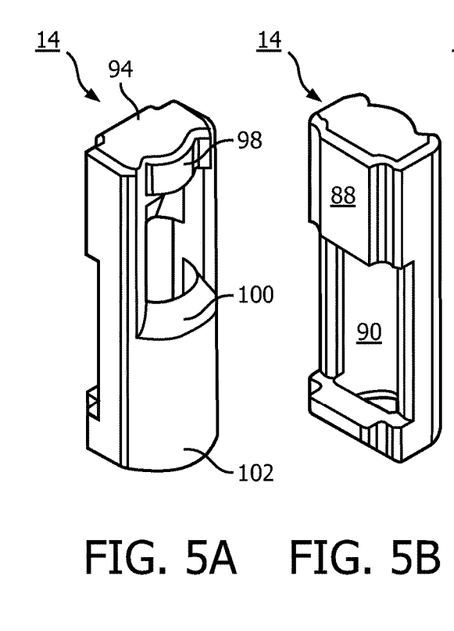
Figure 5C:
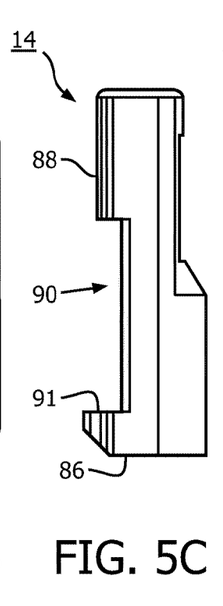
Figure 5D:
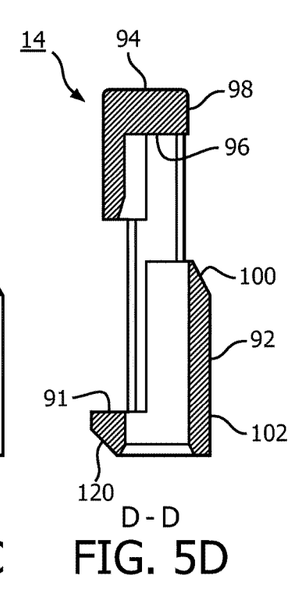
Figure 5E:
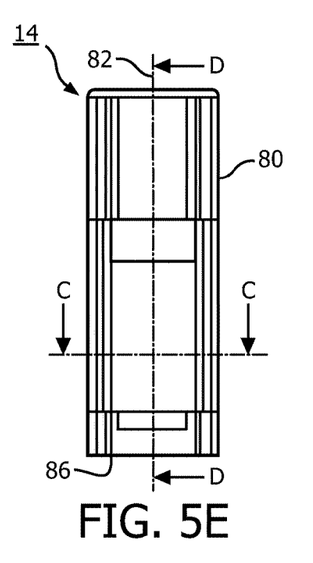
Figure 5F:
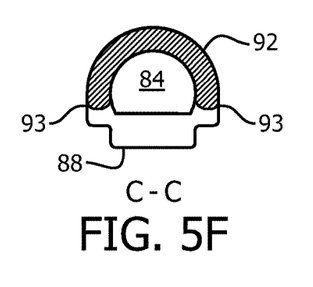

With reference now to FIG. 5, there is shown a right perspective view FIG. 5A, a left perspective view FIG. 5B, a left side view FIG. 5C, a sectional view FIG. 5D along line D-D of an elongated body 80 having a principal axis 82 of the guide sleeve member 14, a transition side view FIG. 5E, and a sectional view along line C-C, transverse to the elongated body 80 of the guide sleeve member 14 according to an embodiment of the present disclosure. The elongated body 80 includes a cavity 84 extending within the elongated body from a distal end 86 of the guide sleeve member 14. The guide sleeve member 14 further includes (i) a first outer surface 88 with an engagement opening 90 disposed inward, along, and transverse to the elongated body 80, and (ii) a second outer surface 92, opposite the first outer surface 88, that comprises a transition surface, wherein the slide member 12 is adapted for moveable insertion, engagement surface 22 first, within the engagement opening 90 of the guide sleeve member 14 and extendable within the guide sleeve member cavity 84. The guide sleeve member 14 together with moveably inserted slide member 12 are adapted for moveable insertion, proximal end first, within the cavity 44 of the neck member 16. As will be discussed further herein below, responsive to insertion of the drive shaft 60 into the cavity 84 of the guide sleeve member 14 together with the moveably inserted slide member 12 within the cavity 44 of the neck member 16 from (a) a first radial position along an axis offset and parallel to the principal axis to (b) a second radial position in-line with the principal axis, via the transition surface 92, the drive shaft 60 is held in frictional contact with the engagement surface 22 of the slide member 12 to enable a reliable transfer of at least one of force and motion from the drive shaft 60 to the neck member 16.

In one embodiment, the cavity 84 of the guide sleeve member 14 extends within the elongated body 80 of the guide sleeve member from the distal end 86 to a proximal end 94 of the guide sleeve member 14. The proximal end of the cavity comprises an end stop 96 for an insertion of the drive shaft 60 within the guide sleeve member 14. See FIG. 5D.

Figure 8A:
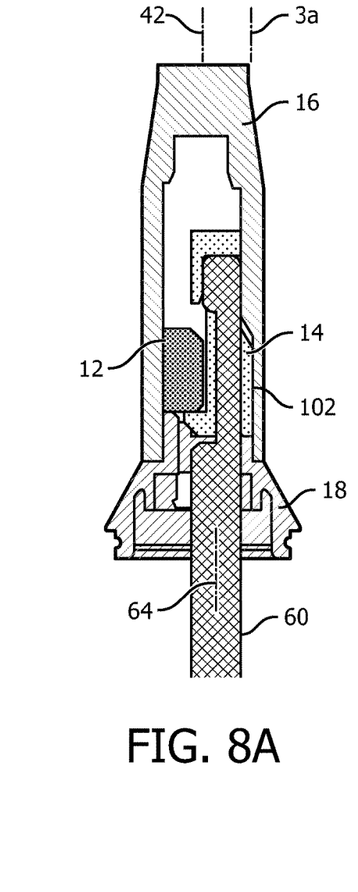
Figure 8B:
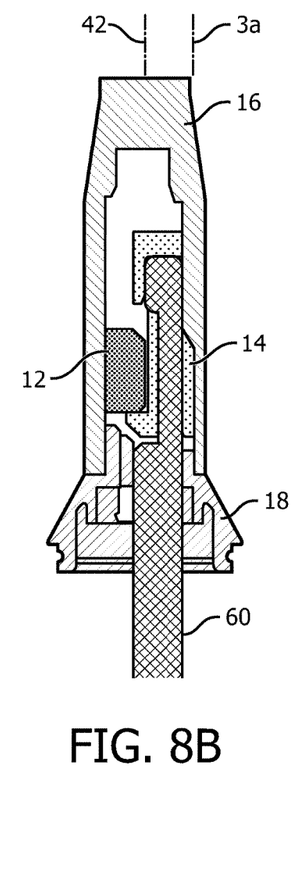
Figure 8C:
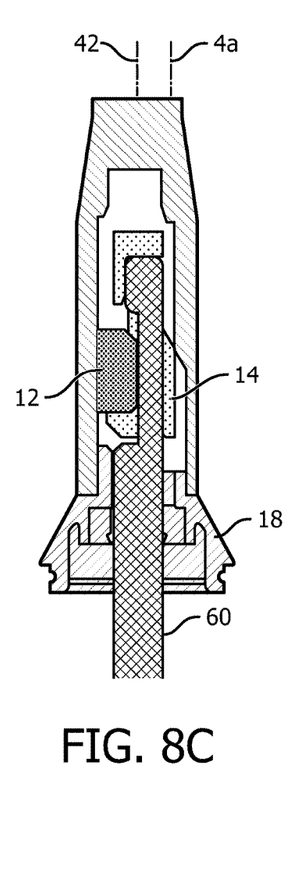
Figure 8D:
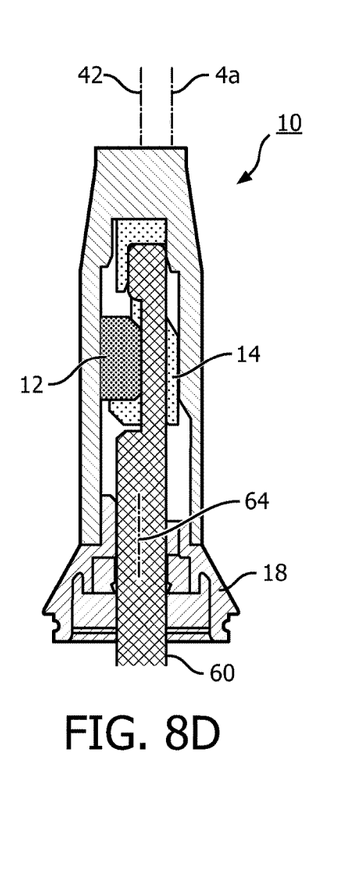
Figure 9A:
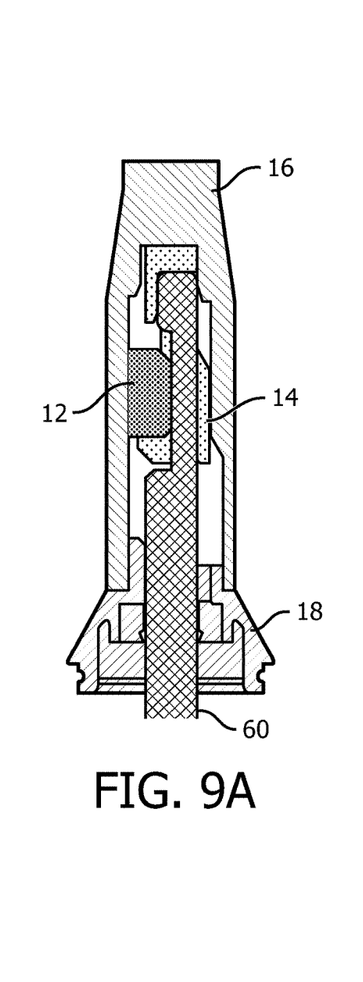
Figure 9B:
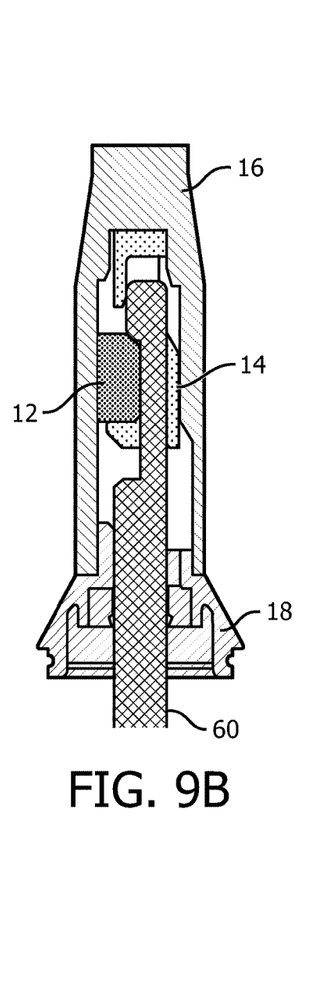
Figure 9C:
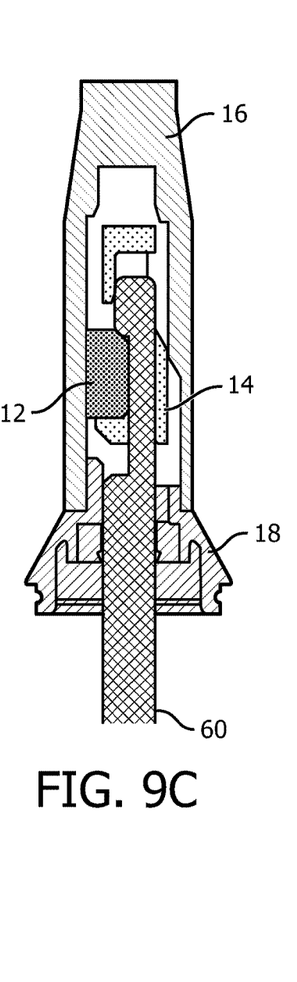
Figure 9D:
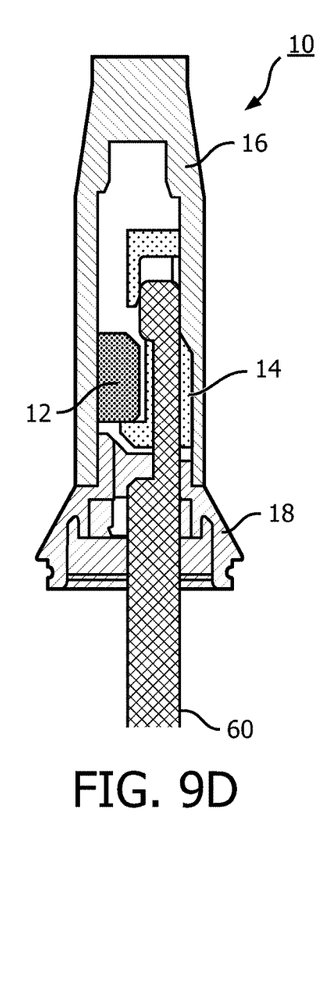

In one embodiment, the transition surface 92 comprises (i) a first portion 98 proximate the proximal end 94 of the guide sleeve member 14, (ii) a transition portion 100 intermediate the proximal and distal ends of the guide sleeve member 14 and (iii) a second portion 102 proximate the distal end 86 of the guide sleeve member 14. The transition portion 100 comprises a circumferential tapered surface moveably fitted for displacement along a complementary tapered surface 106 of a second inner surface 50 of the cavity 44 of the neck member 16. In one embodiment, responsive to a displacement of the circumferential tapered surface 100 along the complementary tapered surface 106, the second portion 102 of the transition surface 92 is moveably displaced between a first radial position along a third axis 3a (see FIGS. 8A and 8B) offset and parallel to the principal axis 42 and a second radial position along a fourth axis 4a (see FIGS. 8C and 8D) offset and parallel to the principal axis, closer to the principal axis 42.

Figure 6A:
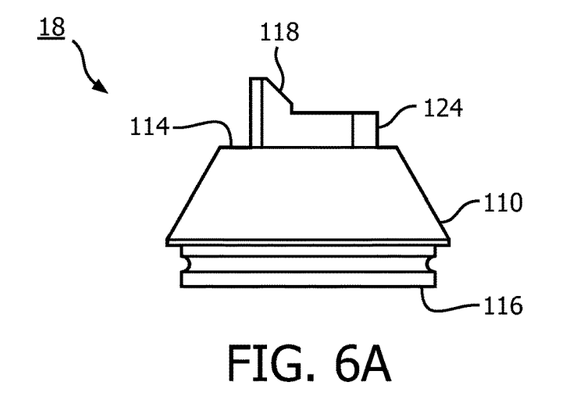
Figure 6B:
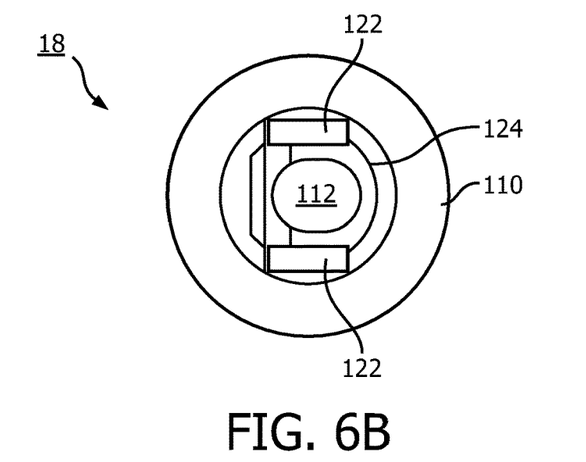
Figure 6C:
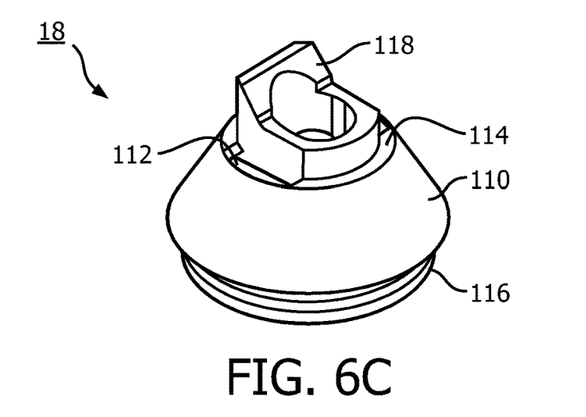

With reference now to FIG. 6, there is shown a side view FIG. 6A, a top view FIG. 6B, and a perspective view FIG. 6C of the collar member 18 according to an embodiment of the present disclosure. The collar member 18 includes a body 110 with a cavity 112 extending therein between a proximal end 114 to a distal end 116. In one embodiment, the proximal end 114 of the collar member 18 is configured to be fixedly attached to the distal end 46 of the neck member 16 for removeably securing the slide member 12 and guide sleeve member 14 within the neck member 16, as will be discussed further herein with reference to FIG. 7.

With reference to FIG. 6B, in one embodiment, the cavity 112 of the collar member 18 comprises, in cross-section, a size sufficient to allow the cross-section of drive shaft 60 to be moveably fitted through the cavity 112 of the collar member 18 (i) along an axis offset and parallel to the principal axis 42 and (ii) in-line with the principal axis 42. In other words, during one portion of an insertion or removal of the drive shaft from the attachment or brush neck assembly 10, the cross-section of drive shaft 60 is moveably fitted through cavity 112 of the collar member 18 along the axis offset and parallel to the principal axis 42. In another portion of the insertion or removal of the drive shaft from the attachment or brush neck assembly 10, the cross-section of drive shaft 60 is moveably fitted through cavity 112 along an axis in-line with the principal axis 42.

In another embodiment, the proximal end 114 of the collar member 18 is adapted for cooperation with a distal end 86 surface of the guide sleeve member 14. For example, the proximal end 114 includes a tapered surface 118 for moveably displacing a complementary tapered surface 120 of the distal end 86 surface of the guide sleeve member 14 to bias the second portion 102 of the transition surface 92 of the guide sleeve member 14 towards the first radial position along the third axis offset and parallel to the principal axis 42 (see FIGS. 8A and 8B). In one embodiment, the collar member 18 further comprises an outer surface 124 at the proximal end 114 thereof that complements an inner surface of the cavity 44 at the distal end 46 of the neck member 16 (see FIGS. 1, 6A-6C, 7A-7D and 8A-8D).

With reference still to FIGS. 6A, 6B and 6C, the proximal end 114 of the collar member 18 further includes at least one attachment aperture 122. As discussed previously, the distal end 46 of the neck member 16 includes at least one pair of resilient attachment tabs 56 (see FIG. 3A). Responsive to insertion of the at least one pair of resilient attachment tabs 56 into the at least one attachment aperture 122, the collar member 18 is fixedly attached to the neck member 16.

Figure 7A:
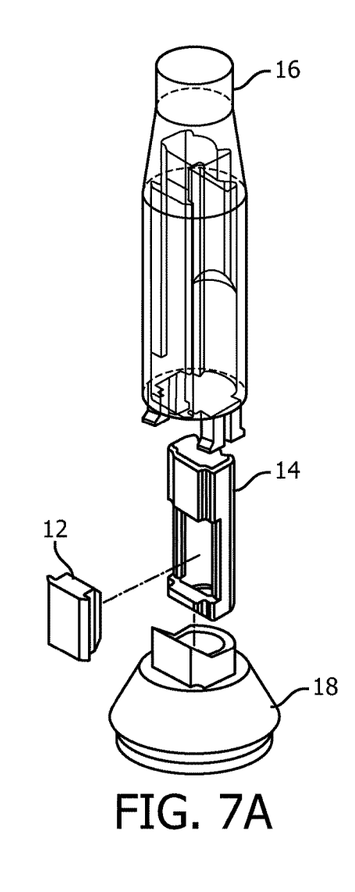
Figure 7B:
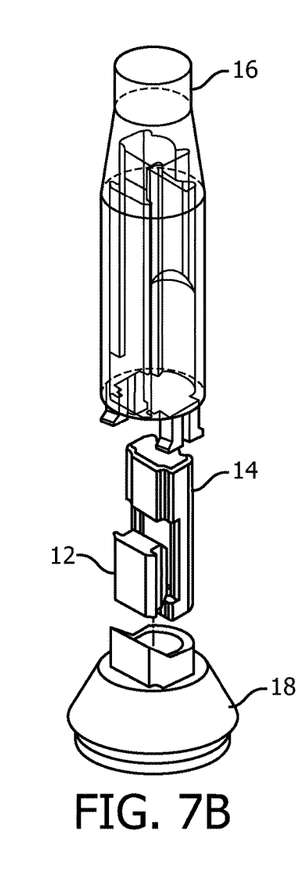
Figure 7C:
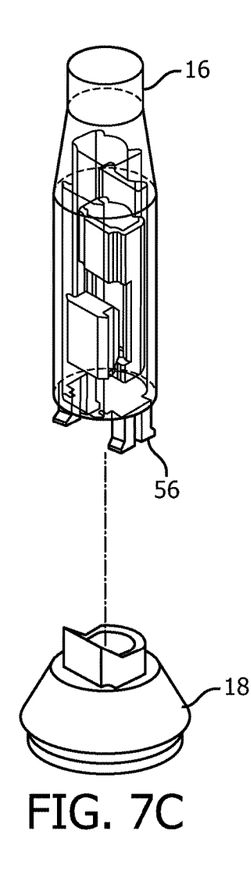
Figure 7D:
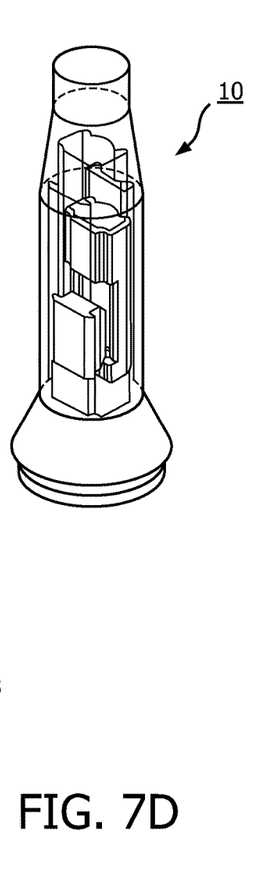

Turning our attention now to FIG. 7, there is shown several exploded perspective views FIG. 7A, FIG. 7B, FIG. 7C and FIG. 7D at various stages of assembly of component parts of the attachment 10 according to an embodiment of the present disclosure. In particular, FIG. 7A illustrates an exploded perspective view of the attachment 10 that includes slide member 12, guide sleeve member 14, neck member 16 and collar member 18. In FIG. 7B, the slide member 12 is moveably inserted, engagement surface 22 first, within the engagement opening 98 of the guide sleeve member 14 and extendable within at least a portion of the guide sleeve member cavity 84. In FIG. 7C, the guide sleeve member 14 together with moveably inserted slide member 12 are moveably inserted, proximal end first, within the cavity 44 of the neck member 16. In addition, responsive to the guide sleeve member 14 together with moveably inserted slide member 12 being moveably inserted, proximal end first, within the cavity 44 of the neck member 16, the linear displacement surface 24 of the slide member 12 is moveably fitted within a slot 49 (FIG. 3B) that extends along the first inner surface 48 of the cavity 44 of the neck member 16. In FIG. 7D, the proximal end 114 of the collar member 18 is fixedly attached to the distal end 46 of the neck member 16 for removeably securing the slide member 12 and guide sleeve member 14 within the neck member 16.

In another embodiment, a toothbrush neck and connecting assembly comprises slide member 12, guide sleeve member 18 and neck member 16. The slide member 12 is placed on the guide sleeve member 18 on a surface 91 (FIGS. 5C and 5D) as shown in FIG. 7B. The slide member 12 having a projection, wherein the projection corresponds to the linear displacement surface 24 and projections (24a, 24b) extending along sides of the linear displacement surface proximate the first set of side surfaces (34, 36) (FIG. 2A) is inserted into the slot 49 of neck member 16. Outer surfaces 93 (FIG. 5F), opposite one another, of guide sleeve member 14 are in sliding contact between the inner surfaces 52 and 54 of the cavity 44 of neck member 16. The outer surface 124 of collar member 18 couples with (and is fixedly attached via the at least one pair of resilient attachment tabs 56 at the distal end 46 of the neck member 16 inserted into the at least one attachment aperture at the proximal end of the collar member 18) an inner surface at the distal end 46 of the neck member 16. The slide member 12 and guide sleeve member 14 will rest on the collar member 18 in an initial position (see FIG. 1).

With reference now to FIG. 8, there is shown sectional views (FIGS. 8A, 8B, 8C, 8D) at various stages of insertion of the drive shaft 60 into the attachment or brush neck assembly 10 according to an embodiment of the present disclosure. FIG. 8A shows an initial position of the attachment or toothbrush neck assembly 10 being inserted onto the drive shaft 60. The top flat face 72 of the drive shaft 60 is in contact with inner surface 96 of the guide sleeve member 14. The attachment or toothbrush neck assembly 10 is then further pushed onto the drive shaft 60, wherein the circumferential tapered surface 100 of the guide sleeve member 14 mates with a matching tapered surface 106 in the neck member 16 (FIG. 8B). The attachment or toothbrush neck assembly 10 is then pushed further down (FIG. 8B to FIG. 8C), wherein the attachment 10 moves right ward until the surfaces 100 and 106 are in contact and then vertically down where the cylindrical surface 102 of guide sleeve member 14 comes in contact with the inner surface 50 (FIGS. 3B and 3C) of the neck member 16. The movement of the attachment or toothbrush neck assembly 10 continues until the top flat surface 94 of guide sleeve member 14 contacts the inner abutment or end surface 47 of the neck member 16. During the movement as illustrated in FIG. 8A to 8D, the flat engagement surface 22 of the slide member 12 comes in frictional contact, and is held in frictional contact, with the notch flat face 66 of the drive shaft 60. As a result, the forces of the moving drive shaft are advantageously transferred, positively, to the toothbrush head via the attachment or toothbrush neck assembly 10.

With reference now to FIG. 9, there is shown sectional views (FIGS. 9A, 9B, 9C, 9D) at various stages of removal of the drive shaft 60 from the attachment or brush neck assembly 10 according to an embodiment of the present disclosure. When the attachment or brush neck assembly 10 is to be removed, the brush neck assembly 10 is simply pulled away from the drive shaft 60, wherein the surface 70 of the notch 66 in the drive shaft 60 will come in contact with the slant face 32 of the slide member 12. When pulled further, the bottom surface 26 of the slide member 12 will push the surface 91 of the guide sleeve member 14, which has a tapered surface 120 that complements the tapered surface 118 of the collar member 18 and moves the attachment or brush neck assembly 10 towards the left, wherein the engagement flat surface 22 loses its frictional engagement with the flat surface of the notch 66 of the drive shaft member 60. The drive shaft then exits the attachment or brush neck assembly 10 along the axis parallel to and offset from the principal axis of the neck member 16.

According to another embodiment, an attachment mountable to an electric toothbrush handle having a drive shaft comprises a neck member, a slide member, a guide sleeve member, and a collar member. The neck member comprises a toothbrush neck and includes an elongated body with a principal axis, the elongated body having a cavity extending within the elongated body from a distal end of the neck member. The slide member comprises (i) an engagement surface and (ii) a linear displacement surface, opposite the engagement surface. The guide sleeve member comprises an elongated body, the elongated body having a cavity extending within the elongated body from a distal end of the guide sleeve member. The guide sleeve member further comprises (i) a first outer surface with an engagement opening disposed inward and transverse to the elongated body, and (ii) a second outer surface, opposite the first outer surface, that comprises a transition surface. The slide member is adapted for moveable insertion, engagement surface first, within the engagement opening of the guide sleeve member and extendable within the guide sleeve member cavity. The guide sleeve member together with the moveably inserted slide member are adapted for moveable insertion, proximal end first, within the cavity of the neck member. The collar member comprises a body with a cavity extending therein between a proximal end to a distal end. The proximal end of the collar member is configured to be fixedly attached to the distal end of the neck member for removeably securing the slide member and guide sleeve member within the neck member. Responsive to insertion of the drive shaft into the cavity of the collar member and the cavity of the guide sleeve member together with the moveably inserted slide member within the cavity of the neck member from (a) a first radial position along an axis offset and parallel to the principal axis to (b) a second radial position in-line with the principal axis, via the transition surface, the drive shaft is held in frictional contact with the engagement surface of the slide member to enable a reliable transfer of at least one of force and motion from the drive shaft to the neck member.

In a still further embodiment, a method for mounting an attachment to an electric toothbrush handle having a drive shaft comprises providing a neck member having an elongated body with a principal axis, the elongated body having a cavity extending within the elongated body from a distal end of the neck member. The method further includes providing a slide member having (i) an engagement surface and (ii) a linear displacement surface, opposite the engagement surface. Still further, the method includes providing a guide sleeve member having an elongated body, the elongated body having a cavity extending within the elongated body from a distal end of the guide sleeve member, the guide sleeve member further having (i) a first outer surface with an engagement opening disposed inward and transverse to the elongated body, and (ii) a second outer surface, opposite the first outer surface, that comprises a transition surface, wherein the slide member is adapted for moveable insertion, engagement surface first, within the engagement opening of the guide sleeve member and extendable within the guide sleeve member cavity, the guide sleeve member together with moveably inserted slide member being adapted for moveable insertion, proximal end first, within the cavity of the neck member. Still further the method includes inserting the drive shaft into the cavity of the guide sleeve member together with the moveably inserted slide member within the cavity of the neck member from (a) a first radial position along an axis offset and parallel to the principal axis to (b) a second radial position in-line with the principal axis, via the transition surface, wherein the drive shaft is held in frictional contact with the engagement surface of the slide member to enable a reliable transfer of at least one of force and motion from the drive shaft to the neck member. In another embodiment, the method further comprises removeably securing, via a collar member, the slide member and guide sleeve member within the neck member, wherein the collar member comprises a body with a cavity extending therein between a proximal end to a distal end, and wherein removeably securing includes fixedly attaching the proximal end of the collar member to the distal end of the neck member.

The measures/device features which are disclosed herein to solve the identified problems, and provide resulting advantages, include one or more of the following: riding over of a conical tapered portion of the brush neck member onto the guide sleeve member; simultaneous, i.e., both axial and radial, movement of the brush neck member (i.e., the brush head assembly) during insertion of the brush neck member over the drive shaft; the frictional force attained between flat surfaces of the drive shaft (i.e., a notch in the drive shaft) and a slide member; and alignment of both brush neck member axis and electric toothbrush handle axis ensure an even distribution of the rotating masses.

Although only a few exemplary embodiments have been described in detail above, those skilled in the art will readily appreciate that many modifications are possible in the exemplary embodiments without materially departing from the novel teachings and advantages of the embodiments of the present disclosure. For example, the embodiments of the present disclosure can be advantageously used in power toothbrush applications. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

In addition, any reference signs placed in parentheses in one or more claims shall not be construed as limiting the claims. The word "comprising" and "comprises," and the like, does not exclude the presence of elements or steps other than those listed in any claim or the specification as a whole. The singular reference of an element does not exclude the plural references of such elements and vice-versa. One or more of the embodiments may be implemented by means of hardware comprising several distinct elements, and/or by means of a suitably programmed computer. In a device claim enumerating several means, several of these means may be embodied by one and the same item of hardware. The mere fact that certain measures are recited in mutually different dependent claims does not indicate that a combination of these measures cannot be used to an advantage.

The invention claimed is:

1. An attachment mountable to an electric toothbrush handle having a drive shaft, the attachment comprising: a neck member having an elongated body with a principal axis, the neck member elongated body having a cavity extending within the neck member elongated body from a distal end of the neck member; a slide member having (i) an engagement surface and (ii) a linear displacement surface, opposite the engagement surface; and a guide sleeve member having an elongated body, the guide sleeve member elongated body having a cavity extending within the guide sleeve member elongated body from a distal end of the guide sleeve member, the guide sleeve member further having (i) a first outer surface with an engagement opening disposed inward and transverse to the guide sleeve member elongated body, and (ii) a second outer surface, opposite the first outer surface, that comprises a transition surface, wherein the slide member is adapted for moveable insertion, engagement surface first, within the engagement opening of the guide sleeve member and extendable within the guide sleeve member cavity, wherein responsive to the attachment being mounted to the drive shaft, the guide sleeve member together with the moveably inserted slide member is adapted for movement within the cavity of the neck member, and the guide sleeve member is adapted for movement within the cavity from (a) a first radial position along an axis offset and parallel to the principal axis to (b) a second radial position in-line with the principal axis, via the transition surface, such that the engagement surface of the slide member is held in frictional contact with the drive shaft to enable a transfer of at least one of force and motion from the drive shaft to the neck member, and the slide member is movable along the principal axis with respect to the guide sleeve member.

2. The attachment of claim 1, wherein the engagement surface of the slide member is held in frictional contact with a notched flat surface of the drive shaft.

3. The attachment of claim 1, wherein the cavity of the guide sleeve member extends within the guide sleeve member elongated body from the distal end to a proximal end of the guide sleeve member, wherein a proximal end of the guide sleeve member cavity comprises an end stop for insertion of the drive shaft within the guide sleeve member.

4. The attachment of claim 1, wherein the linear displacement surface extends along a length dimension of the slide member, wherein responsive to the guide sleeve member together with moveably inserted slide member being moveably inserted, proximal end first, within the cavity of the neck member, the linear displacement surface is moveably fitted within a slot that extends along the first inner surface of the cavity of the neck member.

5. The attachment of claim 1, wherein the transition surface comprises a first portion proximate the proximal end of the guide sleeve member, a transition portion intermediate the proximal and distal ends of the guide sleeve member, and a second portion proximate the distal end of the guide sleeve member, wherein the transition portion comprises a circumferential tapered surface moveably fitted for displacement along a complementary tapered surface of a second inner surface of the cavity of the neck member, wherein responsive to a displacement of the circumferential tapered surface along the complementary tapered surface, the second portion of the transition surface is moveably displaced between a first radial position along a third axis offset and parallel to the principal axis and a second radial position along a fourth axis offset and parallel to the principal axis, closer to the principal axis.

6. The attachment of claim 1, further comprising: a collar member having a body with a cavity extending therein between a proximal end to a distal end, wherein the proximal end of the collar member is configured to be fixedly attached to the distal end of the neck member for removeably securing the slide member and guide sleeve member within the neck member.

7. The attachment of claim 6, wherein the cavity of the collar member comprises, in cross-section, a size sufficient to allow the drive shaft to be moveably fitted through the cavity of the collar member (i) along the axis offset and parallel to the principal axis and (ii) in-line with the principal axis.

8. The attachment of claim 6, further wherein the proximal end of the collar member is adapted for cooperation with a distal end surface of the guide sleeve member, wherein the proximal end includes a tapered surface for moveably displacing a complementary tapered surface of the distal end surface of the guide sleeve member to bias the second portion of the transition surface of the guide sleeve member towards the first radial position along the third axis offset and parallel to the principal axis.

9. The attachment of claim 6, further wherein the proximal end of the collar member includes at least one attachment aperture and wherein the distal end of the neck member includes at least one pair of resilient attachment tabs, wherein responsive to insertion of the at least one pair of resilient attachment tabs into the at least one attachment aperture, the collar member is fixedly attached to the neck member.

10. The attachment of claim 1, wherein the cavity of the neck member further comprises first pair of inner surfaces and a second pair of inner surfaces along a length dimension of the cavity, wherein the first surface of the first pair of inner surfaces comprises a linear translation surface having a slot that extends along the first surface and is adapted for moveably fitting the linear displacement surface of the slide member therein, wherein the engagement surface of the slide member is maintained at a given radial distance from the principal axis in response to the guide sleeve member together with the moveably inserted slide member being moveably fitted within the cavity of the neck member; and the second surface of the first pair of inner surfaces comprises a transition surface configured to complement the transition surface of the guide sleeve member and to enable the drive shaft to be moveably fitted between the first and second radial positions via the transition surface of the guide sleeve member in response to the guide sleeve member being moveably fitted within the cavity of the neck member.

11. The attachment of claim 10, wherein the second pair of inner surfaces comprise guide surfaces for a second pair of outer surfaces of the guide sleeve member, wherein the second pair of outer surfaces of the guide sleeve member are maintained centered about the principal axis in response to the guide sleeve member being moveably fitted within the cavity of the neck member.

12. A method for mounting an attachment to an electric toothbrush handle having a drive shaft, the method comprising: providing a neck member having an elongated body with a principal axis, the neck member elongated body having a cavity extending within the neck member elongated body from a distal end of the neck member; providing a slide member having (i) an engagement surface and (ii) a linear displacement surface, opposite the engagement surface; providing a guide sleeve member having an elongated body, the guide sleeve member elongated body having a cavity extending within the guide sleeve member elongated body from a distal end of the guide sleeve member, the guide sleeve member further having a first outer surface with an engagement opening disposed inward and transverse to the guide sleeve member elongated body, a proximal end, and a second outer surface, opposite the first outer surface, that comprises a transition surface, wherein the slide member is adapted for moveable insertion, engagement surface first, within the engagement opening of the guide sleeve member and extendable within the guide sleeve member cavity, the guide sleeve member together with moveably inserted slide member being adapted for moveable insertion, proximal end first, within the cavity of the neck member; and inserting the drive shaft into the cavity of the guide sleeve member together with the moveably inserted slide member within the cavity of the neck member and moving the guide sleeve member from (a) a first radial position along an axis offset and parallel to the principal axis to (b) a second radial position in-line with the principal axis, via the transition surface, wherein the drive shaft is held in frictional contact with the engagement surface of the slide member to enable a reliable transfer of at least one of force and motion from the drive shaft to the neck member, and the slide member is movable along the principal axis with respect to the guide sleeve member.

13. The method of claim 12, further comprising:
removeably securing, via a collar member, the slide member and guide sleeve member within the neck member, wherein the collar member comprises a body with a cavity extending therein between a proximal end to a distal end, and wherein removeably securing includes fixedly attaching the proximal end of the collar member to the distal end of the neck member.

* * * * *